United States Patent [19]

Russo et al.

[11] Patent Number: 4,935,224
[45] Date of Patent: Jun. 19, 1990

[54] AEROSOL ANTIPERSPIRANT COMPOSITION, INCLUDING SUBSTANTIVITY FLUID, CAPABLE OF BEING DISPENSED AT REDUCED SPRAY RATE, AND PACKAGED AEROSOL ANTIPERSPIRANT

[75] Inventors: Thomas Russo, Andover, N.J.; Therese A. Hayes, Bethlehem, Pa.; Kenneth Klausner, Rockaway, N.J.

[73] Assignee: The Mennen Company, Morristown, N.J.

[21] Appl. No.: 199,267

[22] Filed: May 26, 1988

[51] Int. Cl.[5] .............................................. A61K 7/32
[52] U.S. Cl. ........................................ 424/47; 424/65; 424/78
[58] Field of Search ............................. 424/65, 47, 78

[56] References Cited

U.S. PATENT DOCUMENTS

| | | | |
|---|---|---|---|
| 3,544,258 | 12/1970 | Presant et al. | 424/47 X |
| 3,968,203 | 7/1976 | Spitzer et al. | 424/47 X |
| 4,053,581 | 10/1977 | Pader et al. | 424/68 |
| 4,065,564 | 12/1977 | Miles, Jr. et al. | 424/68 X |
| 4,073,880 | 2/1978 | Pader et al. | 424/68 X |
| 4,152,416 | 5/1979 | Spitzer et al. | 424/65 X |
| 4,423,041 | 12/1983 | Clum et al. | 514/63 X |
| 4,863,721 | 9/1989 | Beck et al. | 424/47 |

FOREIGN PATENT DOCUMENTS

| | | | |
|---|---|---|---|
| 963808 | 3/1975 | Canada | 424/65 |
| 1088428 | 10/1980 | Canada | 424/65 |

Primary Examiner—Ellis P. Robinson
Assistant Examiner—Susan Rucker
Attorney, Agent, or Firm—Antonelli, Terry, Stout & Kraus

[57] ABSTRACT

Disclosed is an aerosol antiperspirant composition containing a silicone polymer (e.g., a silicone gum) and a volatile low-viscosity fluid in which the silicone polymer is soluble, in addition to at least a propellant and an active antiperspirant salt. The silicone polymer is in the composition in an amount of at least 0.1% by weight based on the total weight of the compositoin, and is completely dissolved in the composition. Use of the silicone polymer and the volatile low-viscosity fluid, with the polymer completely dissolved in the composition, avoids dustiness and clogging of the aerosol valve, and permits delivery of the composition at relatively low delivery rates. Where the silicone polymer and volatile low-viscosity fluid are provided as a substantially fluid, product bounce-back upon spraying is further reduced, product deposition is increased, and the deposited product has greater resistance to washing-off and rubbing-off. By delivering the composition from the aerosol package at low delivery rates, product bounce-off is even further reduced, thereby further reducing dusting.

26 Claims, 2 Drawing Sheets

AEROSOL ANTIPERSPIRANT COMPOSITION, INCLUDING SUBSTANTIVITY FLUID, CAPABLE OF BEING DISPENSED AT REDUCED SPRAY RATE, AND PACKAGED AEROSOL ANTIPERSPIRANT

BACKGROUND OF THE INVENTION

The present invention relates to an aerosol antiperspirant composition, delivered to the skin (e.g., the axillae) of a person through use of an aerosol delivery system, and to such composition packaged with the aerosol delivery system. By such an aerosol delivery system, active antiperspirant salts, as part of the composition, are directed to the skin in the form of a finely divided spray.

With aerosol antiperspirants, such as dispersion-type aerosol antiperspirants, a major problem is the dust cloud which arises when the product is sprayed and applied to the skin. This dust cloud causes a major consumer complaint; that is, choking and coughing caused by such dust cloud.

There are two factors which contribute to the development of this dust cloud. The first is the fine dusting initially produced at the site of the actuator button orifice of conventional valves utilized to deliver the finely divided spray. In dispersion-type aerosol antiperspirants delivered by conventional aerosol packaging devices, fine particles are quickly scattered into the air with the expanding propellant(s).

A second factor for the development of the dust cloud is product bounce-off. In currently marketed products, there is low product adhesion during spraying to the underarm area, which results in more product bouncing off and becoming air borne.

Moreover, current products have relatively large valve orifices for the aerosol delivery system and have resulting relatively large spray rates, giving rise to an objectionable "cold" feeling upon application of the product to the skin, and also increasing bounce-off of the product. Such relatively large orifice sizes are necessary to avoid clogging of the orifices.

U.S. Pat. No. 4,152,416 to Spitzer, et al. discloses that with conventional aerosol delivery systems of the vapor tap type, having a button orifice diameter of 0.016 inch, a stem orifide of 0.018 inch in diameter, a vapor tap orifice of 0.023 inch in diameter and a capillary dip tube 0.050 inch in diameter, clogging of the orifices is caused in dispensing an aluminum antiperspirant composition containing dispersed astringent salt particles. Moreover, the vapor tap type of valve requires a high proportion of propellant in the aerosol composition, giving rise to a product that is delivered with a large amount of mistiness and dustiness (that is, the aerosol composition that is dispersed gives rise to stable aerosols of finely divided liquid particles and produces a fine dust). This patent goes on to disclose aerosol antiperspirant compositions capable of dispensing active astringent salt from aerosol containers with low mistiness and dustiness. The astringent salt (such as aluminum chlorhydroxide or other antiperspirant aluminum and/or zirconium salts) is utilized in the antiperspirant composition at relatively high concentrations, yet can be delivered with low mistiness and low dustiness. This patent discloses that the described aerosol antiperspirant compositions include, in combination, an astringent salt in an amount within the range from about 3 to about 30%; a liquid phase comprising a propellant in an amount within the range from about 15% to about 95%; a synthetic polymer gum having a viscosity within the range from about 500,000 to about 100 million centistokes at 25° C., in an amount within the range from about 0.05 to about 5% by weight of the composition, to increase the viscosity of the liquid phase and inhibit mistiness and dustiness; and, optionally, a non-volatile miscible organic liquid in an amount within the range from about 0.1 to about 30% by weight of the composition, of which organic liquid all or part optionally comprises an aliphatic, cycloaliphatic or aromatic carboxylic acid having from about 9 to about 50 carbon atoms that enhances adhesion of the antiperspirant salt to the skin.

This U.S. Pat. No. 4,152,416 further discloses that the polymer gums are either soft or rubbery solids, or highly viscous materials, being soluble in the liquid phase (including the propellant and any non-volatile liquid); and that silicone gums, and especially silicone polymers of the dimethylpolysiloxane type, and acrylic and hydrochloric polymers, are preferred. This patent goes on to disclose that it is important that the polymer gum be soluble in the liquid phase of the composition, and that it is advantageous but not essential that the polymer be soluble in the non-volatile oil component of the composition. The patent goes on to specify that if the polymer is not soluble, and is of a rubbery or soft solid consistency, residues in the valve or actuator button may have a tendency to cause clogging, which can be avoided by adding a lubricant. This patent further discloses that silicone oils are useful lubricants to avoid clogging, and so also may be the non-volatile organic liquid. In the specific examples in this patent, the valve actuator button orifice and the stem orifice are larger than those of the previously discussed conventional vapor tap-type aerosol delivery system. The contents of U.S. Pat. No. 4,152,416 to Spitzer, et al., in its entirety, is incorporated herein by reference.

While disclosing an aerosol antiperspirant composition which avoids some of the grounds of consumer dissatisfaction with aerosol antiperspirants, additional improvements are desired. Thus, there exists a need for improved aerosol antiperspirant compositions, and aerosol delivery systems for delivering such compositions, avoiding various problems still arising in aerosol antiperspirant compositions such as described in U.S. Pat. No. 4,152,416. Specifically, there is still need to provide aerosol antiperspirant compositions wherein bouncing-off of the sprayed product, and an objectionable "cold" feel of the sprayed product, are avoided, and clogging of valves of the aerosol delivery system is avoided. There is also a need to provide an aerosol antiperspirant composition having improved product adhesion (that is, greater adherence of the antiperspirant salt to the skin, with more resistance to the astringent salt washing off or rubbing off of the skin). There also is a need of providing an aerosol antiperspirant composition which can be delivered at a low delivery (spray) rate, while avoiding clogging of the valve. There is also a need for apparatus (for example, an aerosol delivery system) and techniques, used in connection with the composition, so as to avoid the above-mentioned bounce-off problems and objectionable "cold" feel.

U.S. Pat. No. 4,053,581 to Pader, et al. discloses antiperspirant solutions, specifically for a pump spray or roll-on device, containing a mixture of substantially volatile and substantially non-volatile siloxane liquids. This patent discloses that the described solutions can be applied in a manner which is relatively non-tacky and gives the perception of quick drying, and lends lubricity to the pump or roll-on mechanism. This patent discloses that the composition achieving the described objectives includes a solution in alcohol of alcohol-soluble aluminum chlorhydroxide complex, a selected cyclic polyorganoalkyl siloxane compound which is essentially volatile and a selected polyalkyl or poly alkylaryl siloxane compound or polyether siloxane copolymer which are essentially non-volatile. Note also U.S. Pat. No. 4,065,564 to Miles, et al., disclosing an antiperspirant solution specifically for a pump spray or roll-on, containing a substantially non-volatile polyorganosiloxane compound; and U.S. Pat. No. 4,073,880 to Pader, et al., disclosing an antiperspirant solution specifically for a pump spray or roll-on, containing a substantially volatile cyclic polyalkyl siloxane compound.

U.S. Pat. No. 4,423,041 to Clum, et al. discloses compositions comprising a mixture of a silicone fluid (a silicone polymer which is fluid at body temperature and which is insoluble in water and cosmetic oils) and a silicone wax (a silicone polymer which is solid or semi-solid at body temperature and which is insoluble in water and insoluble or only slightly soluble in cosmetic oils) in a ratio of from about 9:1 to 1:3, for use in emulsion-type personal care products such as hand lotions, roll-on and cream deodorants and antiperspirants and the like. This patent discloses that the silicone fluids which are useful include dimethicone, methicone and cyclomethicone; and that the silicone waxes which are useful include stearoxy dimethicone and dimethicone copolyol.

European Patent Application No. 197,485 discloses substantive skin care compositions having resistance to removal from the skin by water-exposure, the composition including an amount of (A) a non-volatile polydihydrocarbylsiloxane component having a viscosity at 25° C. of at least 30 pascal-seconds, and (B) one or more skin care components, the amount of the non-volatile polydihydrocarbylsiloxane component being sufficient to increase the skin-substantivity of at least one of the skin care components. This patent document further discloses, in a preferred embodiment, that the skin care composition contains, in addition to one or more skin care components and a non-volatile polydihydrocarbylsiloxane having a viscosity of at least 30 pascal-second, a volatile polydimethylsiloxane, the amount of the volatile polydimethylsiloxane ranging from 1–99% by weight, based on the weight of non-volatile siloxane plus volatile siloxane. This patent document further discloses that, to provide a pleasing sensation for the user of the compositions, it is preferred to use 25–99% by weight of a volatile polydimethylsiloxane particularly when the non-volatile polydihydrocarbylsiloxane is a gum having a viscosity of at least 10 kPaKs. This patent document further discloses that examples of skin care components which are suitable for the disclosed composition include skin-conditioning components, skin-protecting components, topical medicaments and cosmetic components; and that the cosmetic components include colorants, fragrances, deodorants and decolorants.

While various of U.S. Pat. Nos. 4,053,581 to Pader, et al., 4,065,564 to Miles, et al., 4,073,880 to Pader, et al. and 4,423,041 to Clum, et al., and European Patent Application No. 197,485 disclose compositions, including antiperspirant compositions, containing silicone materials, none of these disclose aerosol antiperspirant compositions. Furthermore, none of these disclose aerosol antiperspirant compositions having improved product adherence to the skin, with greater resistance to washing-off and rubbing-off. Moreover, none of these disclose compositions which can be delivered at reduced spray (delivery) rates, without clogging of the aerosol valve. None of these references even discloses desirability of decreasing the delivery rate so as to avoid the objectionable "cold" feeling upon delivery and to decrease product bounce-off and dustiness.

SUMMARY OF THE INVENTION

Accordingly, it is an object of the present invention to provide an aerosol antiperspirant composition which delivers an antiperspirant active salt from aerosol containers with reduced mistiness and dustiness, while avoiding clogging of the valve of the aerosol container; and to provide an aerosol antiperspirant package constituted by an aerosol container, including an aerosol delivery system, and containing such aerosol antiperspirant composition.

It is a further object of the present invention to provide an aerosol antiperspirant composition delivered by an aerosol delivery system, which delivery system delivers an antiperspirant active salt from aerosol containers at low spray delivery rates without clogging of the valve of the aerosol delivery system. It is a further object of the present invention to provide an aerosol antiperspirant composition having increased active antiperspirant salt deposition (adherence to the skin), with decreased product bouncing off the skin, and with increased resistance to washing-off, and rubbing-off, of the product (antiperspirant active salt) from the skin.

It is a further object of the present invention to provide an aerosol antiperspirant composition, which, when applied using an aerosol delivery system, avoids production of a dust cloud, to thereby avoid problems of choking and coughing arising due to such dust cloud, delivering product at a relatively low spray rate and avoiding clogging of the valve (for example, various valve orifices) of the aerosol package.

The foregoing objects are in part achieved by that aspect of the present invention, wherein a silicone polymer (e.g., a silicone gum) and a volatile low-viscosity fluid, in which the silicone polymer is soluble, is incorporated in the aerosol antiperspirant composition containing at least a propellant and an active antiperspirant salt, with the aerosol antiperspirant composition including at least 0.1% by weight of the silicone polymer, based on the total weight of the composition, and the silicone polymer being completely in solution (dissolved) in the composition (such as in a liquid portion of the composition, for example, in the volatile low-viscosity fluid and propellant). Preferably, the silicone gum is included in the composition in an amount of 0.1% –1.0, more preferably 0.1% –0.5%, by weight based on the total weight of the composition. Illustratively, the silicone polymer can be completely soluble (completely dissolved), in the amounts used in the aerosol composition, in the volatile, low-viscosity fluid. Such an aerosol antiperspirant composition can be delivered at reduced delivery rates without clogging of the valve of the delivery system.

Moreover, the foregoing objects are further achieved by delivering the aerosol antiperspirant composition of the present invention at delivery rates of at most 0.5 gm/sec. Such delivery rate is the delivery rate from a filled aerosol container under conventional pressures (for example, 45-55 psi at 70° F.). By using the specified delivery rate, with the aerosol antiperspirant composition of the present invention, bounce-off of the delivered product from the skin, and dustiness due to the bounce-off, are reduced, without clogging of the valve; moreover, the objectionable "cold" feeling on the skin, due to a relatively large spray rate, is avoided. Furthermore, the spray has a preferred pattern at the lower spray rate.

By the present invention, use of the disclosed aerosol antiperspirant composition, at the disclosed spray rates, achieves objectives of the present invention. Such spray rates can be achieved, using valves with relatively small orifices, without clogging of the valve orifices when using the aerosol antiperspirant composition of the present invention. Notwithstanding the relatively small orifice sizes, clogging of the orifices by either the active antiperspirant salt or the silicone gum is avoided.

Specifically, by utilizing the, e.g., silicone gum in the composition, and even at relatively small sizes of the valve orifices, clogging of the valve of the aerosol container by the active antiperspirant salt is avoided (for example, the active antiperspirant salt can be coated by the gum, so the gum acts as a lubricant for the valve); moreover, since the gum can be completely in solution in the composition clogging of the valve by the gum is avoided. Preferably, the silicone polymer and volatile low-viscosity fluid form a solution of a relatively low viscosity fluid (e.g., between 3,000-8,000 centistokes at 25° C.).

The combination of silicone polymer and volatile low-viscosity fluid, incorporated in the aerosol antiperspirant composition, alters the spray characteristics so that even visually one notes a greatly reduced dustiness.

Furthermore, the objectives of the present invention are achieved by utilizing, as a combination of silicone polymer (e.g., silicone gum) and volatile low-viscosity fluid incorporated in the aerosol antiperspirant composition, a skin substantivity fluid (that is, a fluid that increases adherence to the skin). The skin substantivity fluid is dispersed in the aerosol antiperspirant composition. By incorporating such skin substantivity fluid, of a silicone polymer and volatile low-viscosity fluid in which the silicone polymer is soluble, as part of the aerosol antiperspirant composition, fine dusting initially produced at the site of the aerosol valve (where fine particles are quickly scattered into the air with the expanding propellant) is avoided, while product bounce-off is also avoided. Thus, reduced dustiness of the sprayed composition is achieved, so that choking and coughing produced with application of conventional aerosol antiperspirant compositions, due to the dustiness, is avoided.

Moreover, by use of the substantivity fluid as part of the aerosol antiperspirant composition, product adhesion to the underarm area during spraying is increased, with greater adhesion to the skin and resistance to washing-off and rubbing-off of the product.

As the silicone polymer used in the present invention, silicone gum is particularly noted. These gums are defined in U.S. Pat. No. 4,152,416, the contents of which have already been incorporated by reference. Briefly, this patent discloses incorporating silicone gums, having a viscosity within the range from about 500,000 to about 100 million centistokes at 25° C., as part of the aerosol antiperspirant composition. Such silicone gums (for example, polydimethylsiloxane polymers) as disclosed in U.S. Pat. No. 4,152,416 are also applicable in the present invention. Specific silicone gums include dimethiconol and dimethicone, having the aforedescribed viscosity.

As for the volatile low-viscosity fluid component incorporated into the aerosol antiperspirant composition, various volatile silicone liquids can be utilized. One series of such volatile liquids, which are preferred volatile liquids for the present invention, are the cyclomethicone liquids. However, the present invention is not limited to use of cyclomethicone liquids as the volatile low-viscosity fluid incorporated in the aerosol antiperspirant compositions. Specifically, volatile linear silicone liquids, as well as volatile hydrocarbon liquids, in which the silicone polymer (e.g., silicone gum) is soluble, can be utilized for the present invention. Generally, the volatile low-viscosity liquids usable for the present invention have a boiling point of at least 212° F. (for example, 212° F.-500° F.). Moreover, the volatile low-viscosity liquid should have a viscosity of less than 10 centistokes at 25° C.

As indicated previously, various cyclomethicones can be utilized as the volatile silicone fluid of the present invention. Representative cyclomethicones, each with its flash point and viscosity, are set forth in the following Table 1. Such list set forth in Table 1 is not limiting. All of the materials of Table 1 have a CFTA designation as cyclomethicones.

TABLE 1

| Volatile Fluid | Flash Point (°F.) | Viscosity (Centistoke at 25° C.) |
|---|---|---|
| SWS* F-221 Hexamethyldisiloxane | 30° F. | 0.65 cst @ 25° C. |
| SWS F-222 Decamethyl-cyclopentasiloxane | 157° F. | 4.0 cst @ 25° C. |
| SWS 03314 Octamethyl-cyclotetrasiloxane | 126° F. | 2.3 cst @ 25° C. |
| SWS 251 cyclic dimethylsiloxane | 150° F. | 3.1 cst @ 25° C. |
| Dow Corning 245 | 170° F. | 4.2 cst @ 25° C. |
| Dow Corning 345 | 165° F. | 5.0 cst @ 25° C. |
| Dow Corning 244 | 131° F. | 2.5 cst @ 25° C. |
| Dow Corning 344 | 125° F. | 2.5 cst @ 25° C. |
| Dow Corning 200 Hexamethyldisiloxane | 30° F. | 0.65 cst @ 25° C. |
| Union Carbide VS-7158 | 170° F. | 4.0 cst @ 25° C. |
| Union Carbide VS-7207 | 130° F. | 2.3 cst @ 25° C. |
| Union Carbide VS-7349 | 132° F. | 2.5 cst @ 25° C. |
| General Electric SF-1173 | 130° F. | 2.4 cst @ 25° C. |
| General Electric SF-1202 | 170° F. | 4.1 cst @ 25° C. |
| General Electric SF-1204 | 130° F. | 2.5 cst @ 25° C. |

*SWS Silicones Corporation (Adrian, Michigan)

As can be seen in this Table 1, flash points of these illustrative volatile fluids range from 30° F. to 170° F.

As indicated previously, while various cyclomethicone compounds have been specifically disclosed above as the volatile low-viscosity component incorporated as part of the aerosol antiperspirant compositions of the present invention, the present invention is not limited thereto; and, specifically, low molecular weight straight-chain silicone fluids, as well as volatile hydrocarbon fluids, can be utilized within the scope of the present invention. As the hydrocarbon fluid, various Permethyl hydrocarbons (aliphatic hydrocarbons), products of Permethyl Corporation (Frazer, Pa.) can be utilized. Such hydrocarbons include Permethyl 99A, 101A, 102A and 104A.

As indicated in the foregoing, incorporation of a combination (for example, solution) of silicone gum in volatile low-viscosity fluid, forming a skin substantivity fluid, in aerosol antiperspirant compositions reduces dusting originating at the spray orifice, and also avoids product bounce-off. Moreover, the applied product has increased resistance to being washed off or rubbed off, and has greater adhesion to the skin. Representative substantivity fluids contain a polydimethylsiloxane polymer (e.g., viscosity over 30 million centistokes at 25° C.) and a cyclomethicone to form a low viscosity fluid (between 3,000 to 7,000 centistokes at 25° C.). A specific substantivity fluid usable within the scope of the present invention is Dow Corning Q2-1401 fluid, containing 85-88% by weight cyclomethicone and 12-15% by weight silicone polymer (dimethiconol). Thus, this substantivity fluid contains 100% silicone materials, with 12-15% non-volatile content. This is a preferred substantivity fluid to be used in the present invention. Illustratively, this Dow Corning Q2-1401 fluid can be incorporated in the aerosol antiperspirant composition so as to provide silicone gum levels in the composition of at least 0.1%, preferably 0.1-1.0%, even more preferably 0.1-0.5%, by weight of the total weight of the aerosol antiperspirant composition. At levels of dimethiconol (silicone gum) in the cyclomethicone, in Q2-1401 (that is, 12-15% dimethiconol), the dimethiconol is completely soluble in the cyclomethicone. Generally, dimethiconol can be completely dissolved in cyclomethicone at levels up to 50% by weight. Levels of 0.5% by weight to 6% by weight of the substantivity fluid Q2-1401) (based on the total weight of the composition) incorporated in the aerosol antiperspirant composition increases deposition rate of the antiperspirant active salt.

Another substantivity fluid which can be used in the present invention is General Electric SF-1214. This fluid is a blend of 85% by weight cyclomethicone and 15% by weight silicone gum (dimethicone). This fluid has a viscosity of 4,000-8,000 centistokes at 25° C.

Accordingly, by the present invention, including incorporation of the substantivity fluid in the aerosol antiperspirant composition, dustiness of aerosol antiperspirant compositions upon application to the underarm can be avoided, while delivering the antiperspirant composition at a relatively low delivery rate, avoiding clogging of the valve of the aerosol delivery system and increasing deposition of the active salt.

As indicated previously, the aerosol antiperspirant composition of the present invention includes at least an aerosol propellant and an antiperspirant active salt, in addition to the silicone gum and volatile fluid. Various propellants which can be used are disclosed in U.S. Pat. No. 4,152,416, the contents of which have previously been incorporated by reference, and include chemically inert hydrocarbons such as propane, n-butane, isobutane, and cyclopropane, as well as halogenated hydrocarbons such as dichlorodifluoromethane (Propellant 12), and 1,1-dichloro-1,1,2,2-tetrafluoroethane (Propellant 114), among other known propellants. Further propellants include A-31 propellant (isobutane) and A-46 propellant (a mixture of isobutane and propane and butane).

Antiperspirant aluminum or zirconium salts can be employed in the aerosol antiperspirant compositions of the present invention. Such aluminum and/or zirconium salts are any of those well known in the art, whether soluble or insoluble in the antiperspirant compositions of the invention. Generally, these are acidic inorganic salts of aluminum and zirconium. Examples of such salts are aluminum chlorhydroxide, aluminum chloride, zirconyl hydroxychloride, zirconium oxychloride, and mixtures of these salts, among other such salts. Again, attention is directed to the teachings of U.S. Pat. No. 4,152,416, for description of various aluminum and zirconium salts which can be used in the present invention.

Various other materials conventionally incorporated in aerosol antiperspirant compositions can also be incorporated herein; such materials include bulking agents, to prevent caking or settling out of the astringent salt in the compositions of the invention. Such bulking agent can be a finely divided particulate material, inert and insoluble in the liquids present, having a particle size below 10 microns in diameter. Illustrative bulking agents include colloidal silica and hydrophobic clays.

In addition, customary adjuncts of aerosol antiperspirant compositions, such as perfumes (fragrances), bactericides, fungicides, emollients, and other skin-treating materials can be utilized in the present invention.

The propellant and active antiperspirant salt, as well as the afore-described bulking agent and customary adjuncts, can be incorporated in the aerosol antiperspirant composition of the present invention in amounts as set forth in U.S. Pat. No. 4,152,416.

Other components of aerosol antiperspirant compositions, e.g., as described in U.S. Pat. No. 4,152,416, in amounts as described therein, can also be included in the aerosol antiperspirant compositions of the present invention.

The present aerosol composition can be delivered utilizing aerosol containers with aerosol valves of the vapor tap-type, but having smaller orifice openings (and a resulting decreased delivery rate) than those described in U.S. Pat. No. 4,152,416. Generally, known aerosol valves, but having relatively small orifice sizes, can be used in the present invention. As illustrative of aerosol containers capable of delivering finely-divided sprays, and not limiting, see U.S. Pat Nos. 3,083,917 and 3,083,918 to Abplanalp, et al., and U.S. Pat. No. 3,544,258 to Presant, et al. The contents of each of U.S. Pat. Nos. 3,083,917, 3,083,918 and 3,544,258 are incorporated herein by reference.

DETAILED DESCRIPTION OF THE INVENTION

In the following paragraphs, specific examples of the present invention, utilizing DOW CORNING Q2-1401 and other substantivity fluids, will be disclosed. Of course, as seen from the foregoing, the invention is not limited to use of such substantivity fluids. To the contrary, it is intended to cover all alterations, modifications and equivalents as may be included within the spirit and scope of the invention as defined by the appended claims.

Figure 1:
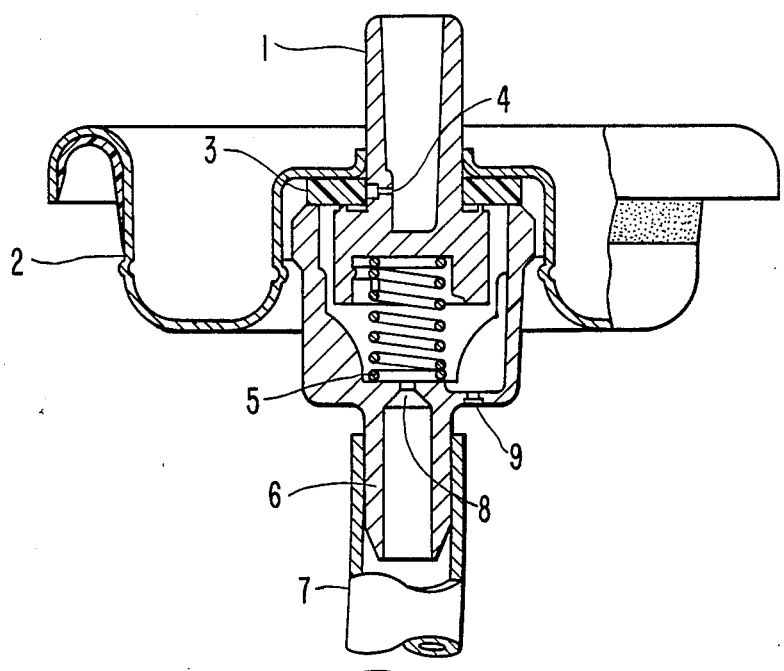
FIG. 1 is an view of a vapor tap-type valve assembly, without the actuator assembly, which can be used as part of the present invention.

FIG. 1 shows a valve assembly usable in the present invention. Stem 1 extends through mounting cup 2 which forms the top of the aerosol container; gasket member 3 acts to close the stem orifice 4 in the absence of downward pressure, to close the valve. Spring 5 forces stem 1 against the gasket member 3, so as to close off the stem orifice 4. The other end of the spring pushes against body 6; in passing from the aerosol container, the composition passes through dip tube 7 into the body 6, the composition passing through the body orifice 8 in the body 6. Then the composition passes into stem 1 through stem orifice 4, and then into actuator button 10 (shown in FIG. 2), and out of the package through button orifice 11 (see FIG. 2). Also shown in FIG. 1 is vapor tap 9.

Figure 2:
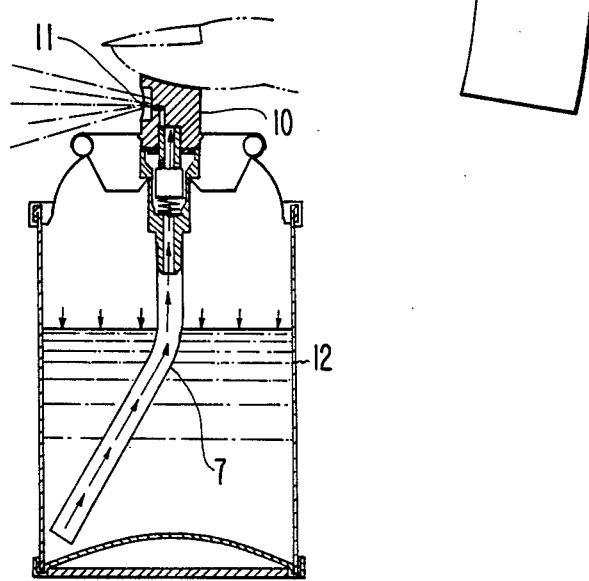
FIG. 2 is a view of an aerosol container of the present invention using the vapor tap type valve of FIG. 1.
Figure 3:
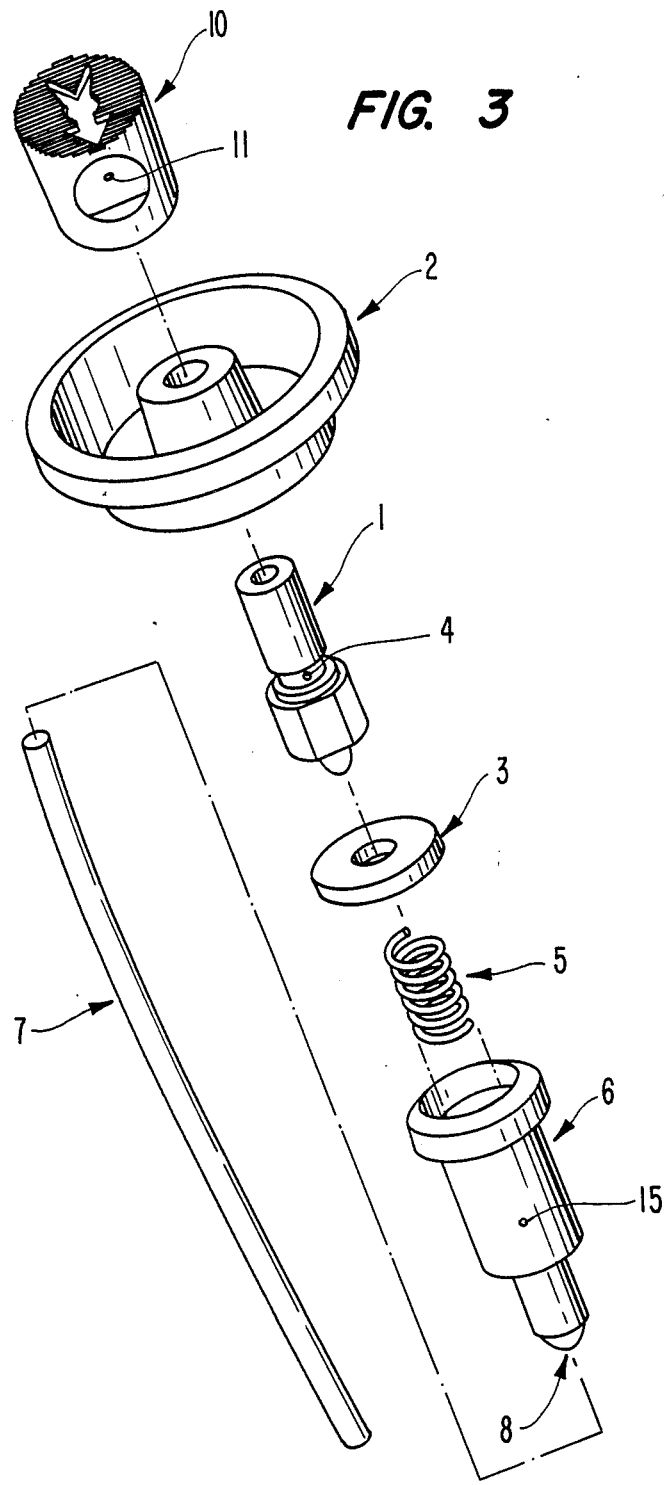
FIG. 3 is an exploded view of a second type of vapor tap-type valve which can be used as part of the present invention.

FIG. 3 shows a different valve assembly, in exploded view. In FIG. 3, the same reference characters, as in FIGS. 1 and 2, have been used to represent the same structure. Note that FIG. 3 shows button orifice 11, and shows vapor tap 15 in the side of body 6. Also shown in FIG. 2 is container 12.

It is preferred to have a relatively small button orifice (e.g. 0.013"–0.020"), in order for the spray to be wide (which is the preferred spray pattern). The stem orifice should also be relatively small, so as to provide a wide spray.

It is important, for purposes of application of a spray of the aerosol antiperspirant composition of the present invention, that the stem and vapor tap orifices be relatively small; these are the orifices which are most important in determining spray rate. Thus, for purposes of the present invention, the stem orifice and vapor tap should be of such a size that the spray (delivery) rate of the aerosol antiperspirant composition is at most 0.5 gm/sec.

A specific example of a preferred valve assembly will now be set forth. Of course, such specific example is illustrative and not limiting; variations, depending, for example, on the specific design of the valve assembly (dependent on the manufacturer) would be within the skill of the art. Thus, using a Seaquist valve, the following orifice sizes were used:

stem orifice: 0.013"
body orifice: 0.018"
vapor tap: 0.013"
button (actuator): an orifice of 0.016"; the button had an insert providing further mechanical break-up of the spray.

Using the above-described valve assembly with an aerosol container loaded with an aerosol antiperspirant composition at a pressure of 45–55 lb./in$^2$ at 70° F., the initial delivery rate was 0.4 gm/sec.

By the present invention, including the relatively low delivery rate and the aerosol antiperspirant composition, the delivery rate can be kept relatively constant, at the relatively low rate, until about 90–95% of the container contents have been emptied, without clogging of the orifices.

Specific examples of compositions within the scope of the present invention will be set forth.

In the following Examples, all percentages of the specified ingredients are weight percentages. Moreover, the DOW CORNING, Q2-1401 fluid contained 87% by weight cyclomethicone and 13% by weight dimethiconol (a polydimethylsiloxane polymer). Where applicable, the designation of the ingredients is the CFTA designation.

EXAMPLE 1

An aerosol antiperspirant composition was prepared having the following formulation:

| EXAMPLE 1 | |
|---|---|
| | % by weight |
| Cyclomethicone | 6.00 |
| Isopropyl palmitate | 2.00 |
| Q2-1401 fluid | 4.00 |
| (cyclomethicone and dimethiconol) | |
| Quaternium-18 Hectorite Gel | 2.00 |
| aluminum chlorohydrate | 10.00 |
| fragrance | 0.50 |
| SD Alcohol 40 | 0.50 |
| | 25.00% concentrate |
| A-31 propellant | 75.00 |
| | 100.00% |

EXAMPLE 2

An aerosol antiperspirant composition was prepared having the following formulation:

| EXAMPLE 2 | |
|---|---|
| | % by weight |
| Cyclomethicone | 9.00 |
| Isopropyl palmitate | 2.00 |
| Q2-1401 fluid | 1.00 |
| Quaternium-8 Hectorite Gel | 2.00 |
| aluminum chlorohydrate | 10.00 |
| fragrance | 0.50 |
| SD Alcohol 40 | 0.50 |
| | 25.00% concentrate |
| A-31 propellant | 75.00 |
| | 100.00% |

The compositions of Example 1 and Example 2 were filled into respective aerosol containers. Upon spraying of such compositions of Example 1 and Example 2, the Example 2 composition exhibited increased visual dusting and a lower deposition rate than that exhibited by the Example 1 composition. Such increased visual dusting and lower deposition rate were the result of the lower concentration of Q2-1401 fluid in the composition of Example 2.

Examples 3–5 give specific aerosol antiperspirant composition formulations.

| EXAMPLE 3 | |
|---|---|
| Cyclomethicone | 8.00 |
| Isopropyl palmitate | 2.00 |
| General Electric SF-1214 | 4.00 |
| (cyclomethicone and dimethicone) | |
| Quaternium-18 Hectorite Gel | 2.00 |
| SD Alcohol 40 | .50 |
| aluminum chlorohydrate | 8.00 |
| fragrance | .50 |
| A-46 propellant | 75.00 |
| | 100.00% |

| EXAMPLE 4 | |
|---|---|
| Permethyl 101A (aliphatic hydrocarbon) | 7.50 |
| Isopropyl myristate | 2.00 |
| Q2-1401 | 3.75 |

-continued
EXAMPLE 4

| | |
|---|---|
| (cyclomethicone and dimethiconol) | |
| Quaternium-18 Hectorite Gel | 1.75 |
| aluminum chlorohydrate | 9.00 |
| SD Alcohol 40 | 0.50 |
| fragrance | 0.50 |
| A-46 propellant | 75.00 |
| | 100.00% |

EXAMPLE 5

| | |
|---|---|
| Permethyl 99A (aliphatic hydrocarbon) | 6.50 |
| Isopropyl myristate | 2.00 |
| General Electric SF-1214 | 4.00 |
| (cyclomethicone and dimethicone) | |
| Quaternium-18 Hectorite Gel | 2.00 |
| aluminum chlorohydrate | 10.00 |
| fragrance | 0.50 |
| A-46 propellant | 75.00 |
| | 100.00% |

COMPARATIVE EXAMPLE 1

| | |
|---|---|
| 245 Fluid (cyclomethicone) | 8.00 |
| Isopropyl palmitate | 2.00 |
| SD Alcohol 40 | 0.50 |
| Bentone Gel VS-5* | 3.00 |
| aluminum chlorohydrate | 10.00 |
| talc | 1.00 |
| fragrance | 0.50 |
| | 25.00% |
| A-31 Propellant | 75.00% |
| | 100.00% |

*a mixture of cyclomethicone, Quaternium-18 Hectorite Gel and SD Alcohol 40

EXAMPLE 6

To test effectiveness of deposition of aerosol antiperspirant compositions of the present invention, as compared with commercial products, the following test was performed. The composition of Example 1 was sprayed for three seconds, at a distance of six inches, against an eight-inch (diameter) watch glass. Also tested were commercial products #1 and #2. The spraying utilized for the commercial products, including the duration of the spray, spray distance and article against which the spray was directed, was the same discussed above with respect to spraying of the composition of Example 1. The results are shown in the following Table 2. For comparison purposes, also shown are the deposition results achieved when spraying the composition of Comparative Example 1, using spraying conditions used in spraying the composition of Example 1. The results shown in Table 2 are the average of six different runs, each utilizing the spray duration, distance and article sprayed against as discussed previously.

TABLE 2

| Product Tested | Product Delivered (gm) | Product Deposited (gm) | % Deposition |
|---|---|---|---|
| Example 1 | .91 | 0.15 | 16.4 |
| Commercial Product #1 | 1.47 | 0.1 | 6.8 |
| Commercial Product #2 | 1.41 | 0.1 | 7.1 |
| Comparative Example 1 | .90 | .05 | 5.5 |

As seen in the foregoing Table 2, the percentage of the product delivered, which is deposited on the watch glass, is much greater for the composition of the present invention, as compared to the compositions of the commercial products and of Comparative Example 1. This shows that the amount of bounce-off and dustiness when applying the composition of the present invention is greatly reduced as compared to those of the tested commercial products and of the composition of Comparative Example 1. Specifically, Example 1 shows a three-fold increase in deposition; such increase is due to the presence of the substantivity fluid (Q2-1401 fluid). The Example 1 composition has a high deposition rate and reduced visual dusting; moreover, use of this composition, including the A-31 propellant, reduces the cold and wet feeling of the product when delivered to the underarm area.

EXAMPLE 7

The composition of Example 6 of U.S. Pat. No. 4,152,416 was tested, in a daily use test, using an aerosol valve assembly and actuator having relatively small orifice sizes, to evaluate clogging; also tested was an aerosol antiperspirant composition within the scope of the present invention. The specific compositions tested are shown in the following:

| Example 6 of U.S. Pat. No. 4,152,416 | |
|---|---|
| | Parts by weight |
| Aluminum chlorhydroxide | 8.0 |
| Isopropyl myristate | 12.8 |
| Silicone gum 10–20 million cst at 25° C. (polydimethyl siloxane) | 0.4 |
| Cab-O-Sil silica | 0.8 |
| propane | 12.0 |
| isobutane | 66.0 |
| | 100.00% |

The composition of the present invention tested was that of Example 1 herein, except that the following was substituted for the 0.50% by weight fragrance of Example 1:

| | % by weight |
|---|---|
| fragrance | 0.3125 |
| Isopropyl palmitate | 0.1875 |

The daily use test was performed according to the following procedure: a plurality of aerosol cans, filled with aerosol composition, after being well shaken were sprayed for 10 secs. twice a day, until the cans were emptied. The weight of each can was recorded before and after spraying, with the delivery rate (in gm/sec.) being recorded for each spraying period. Clogging (or partial clogging, as shown by a decreased delivery rate) was determined. Both the composition according to the present invention and the composition according to Example 6 of U.S. Pat. No. 4,152,416 were sprayed using the following delivery system:

Seaquist Excel 200 "Misty" actuator, having an orifice of 0.016".

Seaquist valve having a stem orifice of 0.013", a body orifice of 0.018" and a vapor tap of 0.013".

Samples of the composition according to the present invention did not exhibit clogging or partial clogging during the daily use test. On the other hand, some of the samples of the composition of Example 6 of U.S. Pat. No. 4,152,416 exhibited a slowdown in delivery rate as the test continued, showing a partial clogging of valve system orifices; other samples of this Example 6 composition showed substantial clogging.

This daily use test showed that the composition according to the present invention avoided clogging of valve assembly orifices, even where the orifices were relatively small; thus, the present composition can be delivered at relatively low delivery rates, through valve assemblies with small orifices, without fear of clogging of the orifices.

Accordingly, the following advantages are achieved by the present invention:

(1) By using an aerosol antiperspirant composition including, in addition to a silicone gum, a volatile low-viscosity fluid (e.g., liquid) in which the gum is soluble, with the gum capable of being completely dissolved in the composition, dustiness while applying the aerosol antiperspirant product can be avoided, and a reduced delivery rate, while avoiding clogging of valves of the aerosol packaging system, can be achieved.

(2) By utilizing a substantivity fluid as the silicone gum and volatile low-viscosity fluid incorporated in the aerosol antiperspirant composition, less bounce-off of the product is achieved, further reducing dustiness; in addition, since there is less dustiness, choking and coughing during application can be reduced.

(3) By utilizing the substantiviry fluid as part of the aerosol antiperspirant composition, a greater deposition rate, greater adhesion to the skin, and greater resistance to washing-off and rubbing-off, of the active antiperspirant salt is achieved.

(4) By decreasing the delivery rate of the aerosol antiperspirant composition of the present invention to a level of at most 0.5 gm/sec., bounce-off of the product is further reduced, thereby further reducing dustiness, and an objectionable cold feeling due to too large a delivery rate can be avoided.

(5) By using the aerosol antiperspirant composition of the present invention as the composition delivered at a reduced rate, the reduced rate can be achieved by decreasing orifice sizes of the valve of the aerosol delivery system, while avoiding clogging of the valve.

While we have shown and described several embodiments in accordance with the present invention, it is understood that the same is not limited thereto but is susceptible of numerous changes and modifications as known to one having ordinary skill in the art and we, therefore, do not wish to be limited to the details shown and described herein, but intend to cover all such modifications as are encompassed by the scope of the appended claims.

What is claimed is:

1. An aerosol antiperspirant composition consisting essentially of an antiperspirant active salt, a propellant, and a combination of a silicone polymer and a volatile low-viscosity fluid which is a solvent for the silicone polymer, the silicone polymer being incorporated in the composition in an amount of at least 0.1% by weight of the total weight of the composition, the silicone polymer being completely dissolved in the composition, whereby the composition can be delivered by an aerosol delivery system, including a valve, at delivery rates of 0.5 gm/sec. or less without clogging of the valve.

2. An aerosol antiperspirant composition according to claim 1, wherein the silicone polymer is a silicone gum included in the composition in an amount in the range of 0.1%–1.0% by weight of the total weight of the composition, and is completely dissolved in the composition.

3. An aerosol antiperspirant composition according to claim 2, wherein the combination of silicone gum and volatile low-viscosity fluid is a substantivity fluid.

4. An aerosol antiperspirant composition according to claim 2, wherein the volatile low-viscosity fluid is a volatile low-viscosity hydrocarbon fluid.

5. An aerosol antiperspirant composition according to claim 2, wherein the volatile low-viscosity fluid is a volatile low-viscosity silicone fluid.

6. An aerosol antiperspirant composition according to claim 5, wherein the silicone gum is a polydimethylsiloxane gum, and the volatile, low-viscosity silicone fluid is a cyclomethicone.

7. An aerosol antiperspirant composition according to claim 6, wherein the polydimethylsiloxane gum is a dimethiconol gum.

8. An aerosol antiperspirant composition according to claim 7, wherein the composition includes 0.5%–6% by weight of said combination.

9. An aerosol antiperspirant composition according to claim 8, wherein the combination includes 12%–15% by weight of the dimethiconol gum and 85%–88% by weight of the cyclomethicone.

10. An aerosol antiperspirant composition according to claim 9, wherein the combination is a substantivity fluid.

11. An aerosol antiperspirant composition according to claim 5, wherein the silicone gum is a dimethicone gum, and the volatile low-viscosity silicone fluid is a cyclomethicone.

12. An aerosol antiperspirant composition according to claim 11, wherein the combination is a substantivity fluid.

13. An aerosol antiperspirant composition according to claim 1, wherein the combination is a substantivity fluid.

14. A packaged aerosol antiperspirant composition, comprising a package of an aerosol antiperspirant composition and an aerosol delivery system, the aerosol delivery system including a valve, wherein the aerosol antiperspirant composition comprises an antiperspirant active salt, a propellant, and a combination of a silicone polymer and a volatile low-viscosity fluid which is a solvent for the silicone polymer, the silicone polymer being incorporated in the composition in an amount of at least 0.1% by weight of the total weight of the composition, the silicone polymer being completely dissolved in the composition, whereby the aerosol antiperspirant composition can be delivered by said aerosol delivery system, including the valve, at delivery rates of 0.5 gm/sec. or less without clogging of the valve; and wherein said valve of the aerosol delivery system has an orifices constituting an outlet for the aerosol antiperspirant composition out of the package, the orifices having sizes such that the delivery rate of the aerosol antiperspirant composition from the package is at most 0.5 gm/sec.

15. A packaged aerosol antiperspirant composition according to claim 14, wherein said orifices include an orifice in a stem of the valve and a vapor tap orifice, the sizes of the stem orifice and vapor tap orifice being such that the delivery rate of aerosol antiperspirant composition is at most 0.5 gm/sec.

16. A packaged aerosol antiperspirant composition according to claim 14, wherein the aerosol delivery system includes a button orifice, the button orifice being in the range of 0.083"-0.020" in diameter.

17. A packaged aerosol antiperspirant composition according to claim 14, wherein the aerosol antiperspirant composition is included in the package at a pressure of 45-55 psi.

18. A method of applying an aerosol antiperspirant, comprising delivering the aerosol antiperspirant composition from the packaged antiperspirant composition according to claim 14 by opening the valve, the aerosol antiperspirant composition being delivered at a delivery rate of at most 0.5 gm/sec.

19. An aerosol antiperspirant composition according to claim 1, wherein the silicone polymer is completely dissolved in the volatile low-viscosity fluid.

20. An aerosol antiperspirant composition according to claim 19, wherein the silicone polymer is a silicone gum, and the volatile low-viscosity fluid is a volatile low-viscosity silicone fluid.

21. An aerosol antiperspirant composition according to claim 20, wherein said volatile low-viscosity silicone fluid is a cyclomethicone.

22. A packaged aerosol antiperspirant composition according to claim 14, wherein the aerosol antiperspirant composition consists essentially of the antiperspirant active salt, the propellant, and the combination of the silicone polymer and the volatile low-viscosity fluid, with the silicone polymer being completely dissolved in the composition.

23. A packaged aerosol antiperspirant composition according to claim 14, wherein the package further comprises a can for holding the aerosol antiperspirant composition, the aerosol antiperspirant composition being maintained under pressure in the can, the aerosol delivery system constituting the sole outlet for the aerosol antiperspirant composition from the can.

24. A packaged aerosol antiperspirant composition according to claim 14, wherein the silicone polymer is completely dissolved in the volatile low-viscosity fluid.

25. A packaged aerosol antiperspirant composition according to claim 24, wherein the silicone polymer is a silicone gum, and the volatile low-viscosity fluid is a volatile low-viscosity silicone fluid.

26. A packaged aerosol antiperspirant composition according to claim 25, wherein the low-viscosity silicone fluid is cyclomethicone.

* * * * *